United States Patent [19]

Chan

[11] Patent Number: 4,728,669

[45] Date of Patent: Mar. 1, 1988

[54] FUNGICIDAL 3-(N-ACYL-N-ARYLAMINO)-GAMMA-BUTYROLACTONES AND GAMMA-BUTYROTHIOLACTONES

[75] Inventor: David C. K. Chan, Petaluma, Calif.

[73] Assignee: Chevron Research Company, San Francisco, Calif.

[21] Appl. No.: 13,856

[22] Filed: Feb. 22, 1979

Related U.S. Application Data

[63] Continuation-in-part of Ser. No. 847,502, Nov. 1, 1977, abandoned, which is a continuation-in-part of Ser. No. 837,121, Sep. 29, 1977, Pat. No. 4,141,989, which is a continuation-in-part of Ser. No. 731,491, Oct. 12, 1976, Pat. No. 4,107,323, which is a continuation-in-part of Ser. No. 631,351, Nov. 12, 1975, Pat. No. 4,012,519, which is a continuation-in-part of Ser. No. 548,660, Feb. 10, 1975, Pat. No. 3,933,860.

[51] Int. Cl.$^4$ .................. A01N 43/08; C07D 307/30
[52] U.S. Cl. .................................... 514/472; 549/321
[58] Field of Search .................... 260/343.6; 424/279; 549/421, 321; 514/472

[56] References Cited

U.S. PATENT DOCUMENTS

| | | | |
|---|---|---|---|
| 4,143,155 | 3/1979 | Hubele et al. | 260/343.6 |
| 4,233,308 | 11/1980 | Kunz et al. | 549/321 |
| 4,440,780 | 4/1984 | Chan | 549/321 |

FOREIGN PATENT DOCUMENTS

| | | | |
|---|---|---|---|
| 0033516 | 8/1981 | European Pat. Off. | 549/321 |
| 2350944 | 4/1974 | Fed. Rep. of Germany . | |
| 724786 | 5/1977 | Fed. Rep. of Germany | 260/343.6 |
| 827671 | 8/1975 | France . | |
| 2006783 | 5/1979 | United Kingdom | 549/321 |

OTHER PUBLICATIONS

American Petroleum Institute; API Patent Alert, 12/29/75; Selected abstracts from Derwent CPI Issue No. W43; p. 5.

Derwent Publications Ltd.; Central Patents Index; 6/7/74, Week V18 32,652V–34,499V; p. 32973V.

*Primary Examiner*—Nicky Chan
*Attorney, Agent, or Firm*—S. R. La Paglia; R. C. Gaffney; L. S. Squires

[57] ABSTRACT

3-(N-acyl-N-arylamino)-gamma-butyrolactones and thiobutyrolactones have fungicidal activity.

10 Claims, No Drawings

FUNGICIDAL 3-(N-ACYL-N-ARYLAMINO)-GAMMA-BUTYROLACTONES AND GAMMA-BUTYROTHIOLACTONES

RELATED APPLICATIONS

This application is a continuation-in-part of application Ser. No. 847,502, filed Nov. 1, 1977, and now abandoned, which in turn is a continuation-in-part of application Ser. No. 837,121, filed Sept. 29, 1977, now U.S. Pat. No. 4,141,989, which in turn is a continuation-in-part of application Ser. No. 731,491, filed Oct. 12, 1976, now U.S. Pat. No. 4,107,323, which in turn is a continuation-in-part of application Ser. No. 631,351, filed Nov. 12, 1975, now U.S. Pat. No. 4,012,519, which in turn is a continuation-in-part of application Ser. No. 548,660, filed Feb. 10, 1975, now U.S. Pat. No. 3,933,860, the disclosures of which are incorporated herein by reference.

DESCRIPTION OF THE PRIOR ART

U.S. Pat. No. 3,933,860, issued to David Cheong King Chan on Jan. 26, 1976, and U.S. Pat. No. 4,012,519, issued to David Cheong King Chan on Mar. 15, 1977, disclose the use of a large class of 3-(N-acyl-N-arylamino) lactones and 3-(N-acyl-N-arylamino) lactams as protectant fungicides.

U.S. Pat. No. 4,034,108, issued July 5, 1977, to H. Moser, and U.S. Pat. No. 4,015,648, issued May 24, 1977 to H. Moser, disclose the use of N-(methoxycarbonylethyl)-N-haloacetylanilines as preventive and curative fungicides.

German Patent Publication Nos. 2,643,403 and 2,643,445, published Apr. 7, 1977, discloses the use of N-(alkylthiocarbonylethyl)acetanilides for controlling fungi, particularly those of the class Phycomycetes.

Netherlands Patent Publication No. 152,849, published Apr. 15, 1977, discloses the use of N-(alkoxymethyl)acetanilides as fungicides.

SUMMARY OF THE INVENTION

It has now been found that 3-(N-acyl-N-arylamino)-gamma-butyrolactones and butyrothiolactones are effective for the control of fungi, especially for downy mildew fungal infection caused by fungal species of the Peronosporaceae family and late blight fungal infection caused by *Phytophthora infestans*. Some of the compounds of the invention are effective both as protectant fungicides, i.e., they prevent or protect against fungal infections, and as eradicant fungicides, i.e., they eliminate and cure established infections. The compounds of the invention are especially preferred for the control of grape downy mildew.

DESCRIPTION OF THE INVENTION

The compounds of the invention are represented by the Formula (I)

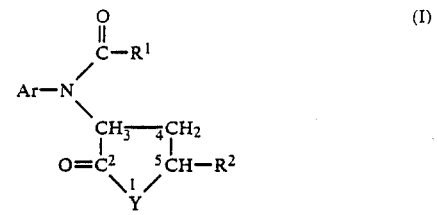

wherein Ar is phenyl, naphthyl, or phenyl or naphthyl substituted with 1 to 4 of the same or different substituents selected from fluoro, chloro, bromo, alkyl of 1 to 4 carbon atoms or alkoxy of 1 to 4 carbon atoms; $R^1$ is hydroxymethyl, halomethyl of 1 to 3 of the same or different halogens selected from fluoro, chloro or bromo, alkoxymethyl of 1 to 6 carbon atoms, alkylthiomethyl of 1 to 6 carbon atoms, phenylthiomethyl, phenoxymethyl, phenylthiomethyl or phenoxymethyl substituted on the phenyl ring with 1 to 2 of the same or different substituents selected from fluoro, chloro, bromo, alkyl of 1 to 4 carbon atoms or alkoxy of 1 to 4 carbon atoms, cycloalkyl of 3 to 6 carbon atoms, cycloalkyl of 3 to 6 carbon atoms substituted with 1 to 4 of the same or different substituents selected from alkyl of 1 to 4 carbon atoms, fluoro, chloro, bromo, hydroxy or alkoxy of 1 to 4 carbon atoms; and $R^2$ is hydrogen, chloro, bromo, alkyl of 1 to 6 carbon atoms, phenyl or phenyl substituted with 1 to 2 of the same or different substituents selected from fluoro, chloro, bromo or alkyl of 1 to 6 carbon atoms; and Y is O or S, with the proviso that when Ar is phenyl or substituted phenyl and $R^1$ is halomethyl, Y is not O.

Representative substituted-phenyl groups which Ar may represent are 2-fluorophenyl, 2,4-dichlorophenyl, 3,5-dibromophenyl, 4-methylphenyl, 2,6-diethylphenyl, 4-methoxyphenyl, 4-nitrophenyl, 2,6-dimethyl-4-chlorophenyl, 2,3,6-trimethylphenyl, 2,3,5,6-tetramethylphenyl. Preferred substituted-phenyl Ar groups are phenyl substituted with 1 to 2 of the same or different substituents selected from chloro, bromo, alkyl of 1 to 4 carbon atoms or alkoxy of 1 to 4 carbon atoms. Most preferred substituted-phenyl Ar groups are 2,6-dialkylphenyl, especially 2,6-dimethylphenyl.

Representative substituted-naphthyl Ar groups are 1-naphthyl, 2-naphthyl, 1-methyl-2-naphthyl, 4-methyl-2-naphthyl, 4-methyl-1-naphthyl, 2-chloro-1-naphthyl, 2-methoxy-1-naphthyl, 2,4-dimethyl-1-naphthyl and 2,7-dimethyl-1-naphthyl. Preferred substituted naphthyl Ar groups are 2-alkyl-1-naphthyl groups, especially 2-methyl-1-naphthyl.

Representative halomethyl groups which $R^1$ may represent include fluoromethyl, chloromethyl, bromomethyl, dichloromethyl, tribromomethyl and fluorodichloromethyl. The preferred halomethyl $R^1$ group is chloromethyl.

Representative alkoxymethyl $R^1$ groups are methoxymethyl, ethoxymethyl, isopropoxymethyl and n-pentoxymethyl. The preferred alkoxymethyl $R^1$ group is methoxymethyl.

Representative alkylthiomethyl $R^1$ groups are methylthiomethyl, n-propylthiomethyl and n-pentylthiomethyl.

Representative cycloalkyl of $R^1$ groups are cyclopropyl, cyclobutyl, cyclopentyl, cyclohexyl, and 4-methylcyclohexyl.

Representative substituted-phenylthiomethyl and substituted-phenoxymethyl R¹ groups are 4-chlorophenylthiomethyl, 4-methylphenoxymethyl, 2,4-dichlorophenoxymethyl, 3,5-dimethylphenylthiomethyl and 2-chloro-4-methylphenoxymethyl.

Representative alkyl R² groups are methyl, ethyl, isopropyl and n-hexyl. Representative substituted-phenyl R² groups are 2-chlorophenyl, 2,4-dichlorophenyl, 4-methylphenyl and 2,3-dimethylphenyl.

Preferably Ar is phenyl substituted with 1 to 2 of the same or different substituents selected from fluoro, chloro, bromo or alkyl of 1 to 2 carbon atoms, or 2-alkyl-1-naphthyl. The most preferred Ar groups are 2,6-dimethylphenyl or 2-methyl-1-naphthyl.

Preferably R¹ is alkoxymethyl of 1 to 6 carbon atoms, chloromethyl or bromomethyl. Most preferably R¹ is methoxymethyl or chloromethyl.

Preferably R² is hydrogen or methyl.

The N-phenylamino- and N-substituted phenylaminothiolactones of the invention may be represented by the formula

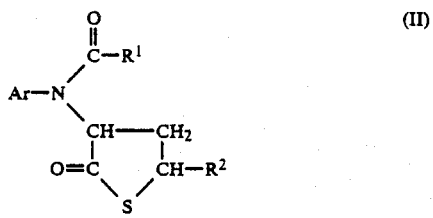

(II)

wherein Ar is phenyl or substituted phenyl as previously defined, and R¹ and R² have the same significance as previously defined. In formula (II), Ar preferably is phenyl substituted with 1 to 2 of the same or different substituents selected from fluoro, chloro, bromo, alkyl of 1 to 4 carbon atoms or alkoxy of 1 to 4 carbon atoms. A preferred class of N-phenylamino- and N-substituted phenylaminothiolactones is that represented by the formula

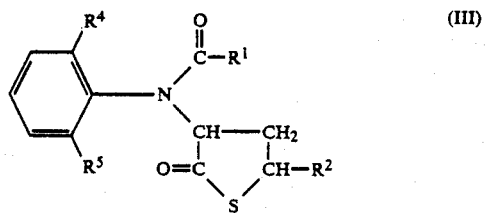

(III)

wherein R¹ is chloromethyl or alkoxymethyl of 1 to 4 carbon atoms, R² is hydrogen or methyl, and R⁴ and R⁵ individually are methyl or ethyl. Particularly preferred compounds of formula (III) are those wherein R¹ is chloromethyl or methoxymethyl, R² is hydrogen and R⁴ and R⁵ are methyl.

The N-phenylamino and N-substituted-phenylaminolactones of the invention may be represented by the formula

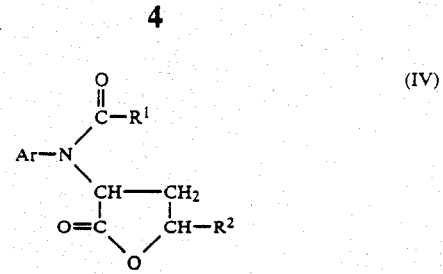

(IV)

wherein Ar is phenyl or substituted phenyl as previously defined, R² has the same significance as previously defined, and R¹ is hydroxymethyl, alkoxymethyl of 1 to 6 carbon atoms, alkylthiomethyl, phenylthiomethyl, phenoxymethyl, or phenylthiomethyl or phenoxymethyl substituted on the phenyl ring with 1 to 2 of the same or different substituents selected from fluoro, chloro, bromo, alkyl of 1 to 4 carbon atoms or alkoxy of 1 to 4 carbon atoms. A preferred class of N-phenylamino- and N-substituted-phenylaminolactones is that represented by the formula

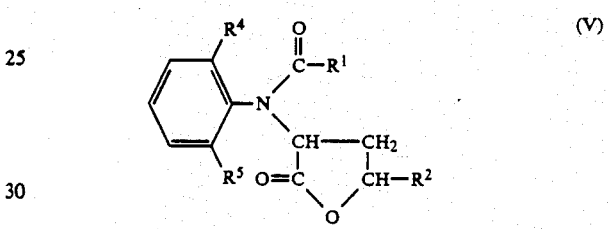

(V)

wherein R¹ is alkoxymethyl of 1 to 4 carbon atoms, R² is hydrogen or methyl, and R⁴ and R⁵ individually are methyl or ethyl. Preferred compounds of formula (V) are those wherein R¹ is methoxymethyl, R² is hydrogen, and R⁴ and R⁵ are methyl.

The N-naphthylamino- and N-substituted naphthylaminolactones and thiolactones of the invention may be represented by the formula

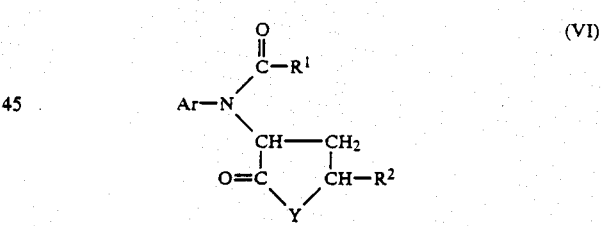

(VI)

wherein Ar is naphthyl or substituted naphthyl, and wherein R¹, R² and Y have the same significance as previously defined. A preferred class of N-naphthyl and N-naphthyl-substituted-aminolactones and thiolactones is that represented by the formula (VII)

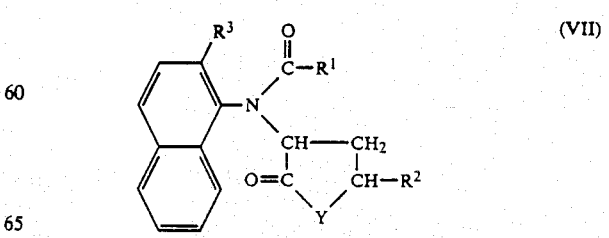

(VII)

wherein R¹ is chloromethyl, bromomethyl or alkoxymethyl of 1 to 4 carbon atoms; R³ is hydrogen or alkyl of 1 to 3 carbon atoms; and Y is oxygen or sulfur. Particularly preferred compounds of formula (VII) are those wherein $R^1$ is chloromethyl or alkoxymethyl, $R^3$ is methyl and Y is oxygen.

Representative compounds of formula (I) include:

3-(N-bromoacetyl-N-phenylamino)-gamma-butyrothiolactone 3-(N-isopropoxyacetyl-N-4-chlorophenylamino)-gamma-butyrothiolactone 3-(N-phenoxyacetyl-N-4-methoxyphenylamino)-gamma-butyrothiolactone 3-(N-chloroacetyl-N-2,6-dimethylphenylamino)-5-methyl-gamma-butyrothiolactone 3-(N-dichloroacetyl-N-2,6-dimethylphenylamino)-gamma-butyrothiolactone 3-(N-hydroxyacetyl-N-3,4-dimethylphenylamino)-gamma-butyrothiolactone 3-(N-chloroacetyl-N-4-methylphenylamino)-5-chloro-gamma-butyrothiolactone 3-(N-hydroxyacetyl-N-2-methoxyphenylamino)-gamma-butyrolactone 3-(N-chloroacetyl-N-2-methylnaphth-1-ylamino)-5-phenyl-gamma-butyrothiolactone 3-(N-methoxyacetyl-N-2-methylnaphth-1-ylamino)-gamma-butyrothiolactone 3-(N-chloroacetyl-N-1-naphthylamino)-5-methyl-gamma-butyrothiolactone 3-(N-hydroxyacetyl-N-2-methylnaphth-1-ylamino)-gamma-butyrolactone and 3-(N-acetoxyacetyl-N-2-methylnaphth-1-ylamino)-gamma-butyrolactone 3-(N-cyclopropylcarbonyl-N-2,6-dimethylphenylamino)-gamma-butyrolactone.

The lactone and thiolactone compounds of the invention may be prepared by alkylating an aniline (VIII) with an alpha-halo-gamma-butyrolactone or alpha-halo-gamma-butyrothiolactone (IX) and subsequently acylating the alpha-(N-arylamino)-gamma-butyrolactone or butyrothiolactone (X) with an acyl halide (XI) to give the 3-(N-acyl-N-arylamino)-gamma-butyrolactone or butyrothiolactone product (I), as depicted by the following equations:

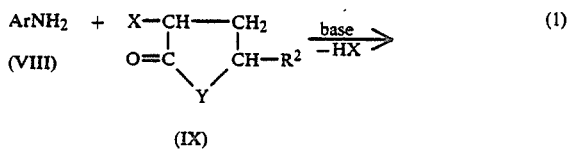

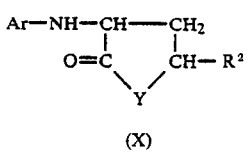

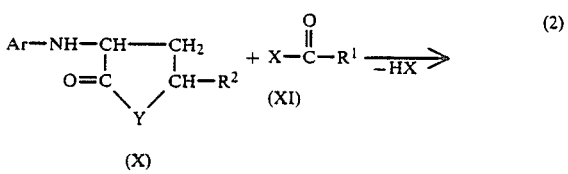

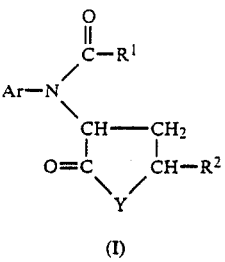

wherein Ar, $R^1$, $R^2$ and Y have the same significance as previously defined, and X is chloro or bromo.

The alkylation reaction (1) is conducted in the presence of a base. Suitable bases are inorganic alkali metal carbonates such as sodium carbonates or potassium carbonate or organic amines such as trialkylamines, e.g., triethylamine, or pyridine compounds, e.g., pyridine or 2,6-dimethylpyridine. Generally, substantially equimolar amounts of reactants (VIII) and (IX) and the base are employed. In one modification of the reaction, a molar excess of the aniline reactant (VIII) is used as the base, and no additional base is employed. The reaction is conducted in inert organic solvents, e.g. apolar diprotic solvents such as dimethylformamide and acetonitrile and aromatic hydrocarbons such as benzene and toluene, at reaction temperatures varying from 25° C. to 150° C., preferably from 50° C. to 150° C. Water may be employed as a co-solvent. The reaction pressure may be atmospheric, subatmospheric or superatmospheric. However, for convenience of conducting the reaction, the pressure is generally atmospheric. The reaction time will, of course, vary depending upon the reactants and the reaction temperature. Generally the reaction time is from 0.25 to 24 hours. The product (X) is generally purified by conventional procedures, e.g., extraction, distillation or crystallization, before use in the acylation reaction (2).

Preferred alkylation reaction conditions are given in more detail in the commonly assigned application of Richard N. Reynolds, Jr., entitled "Alkylation of Aniline with a Lactone in the Presence of Water", Ser. No. 847,503, filed Nov. 1, 1977.

The acylation reaction (2) is conducted by conventional procedures. The reactants (X) and (XI) are generally contacted in substantially equimolar amounts in an inert organic solvent at a temperature of 0° to 100° C. Suitable inert organic solvents include ethyl acetate, methylene dichloride, dimethoxyethane, benzene, etc. The product is isolated and purified by conventional procedures such as extraction, distillation, chromatography, crystallization, etc.

When preparing a butyrolactone product (compounds of Formula (I) wherein Y=O), an organic amine such as a trialkylamine or a pyridine compound may be employed as an acid acceptor. However, when preparing a butyrothiolactone product (compounds of Formula (I) wherein Y=S), an organic amine should not be employed.

Preferred acylation reaction conditions are given in more detail in the commonly assigned application of Richard N. Reynolds, Jr., Stephen D. Ziman and David C. K. Chan, entitled "Acylation of Lactone-Substituted Aniline Compound in the Absence of an Acid Acceptor", Ser. No. 847,504, filed Nov. 1, 1977.

The compounds of Formula (I) wherein $R^1$ is alkylthiomethyl, phenylthiomethyl or substituted-phenylthiomethyl may be prepared from the corresponding compound wherein $R^1$ is halomethyl by reacting the corresponding halomethyl compound with an alkali metal mercaptide by conventional procedures as depicted in the following equation (3):

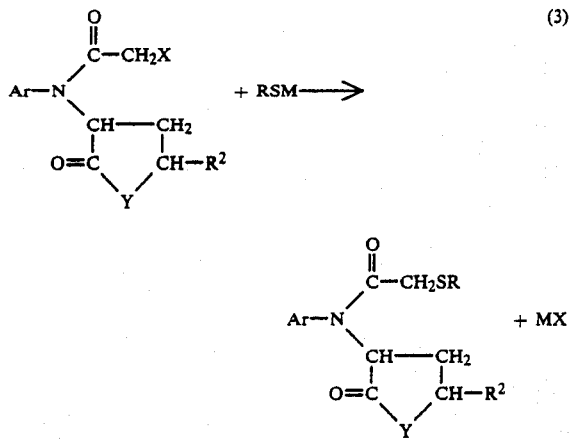

wherein Ar, $R^2$, X and Y are as previously defined, M is alkali metal, R is alkyl, phenyl or substituted phenyl. In reaction (3), Y preferably is oxygen.

The compounds of Formula (I) wherein $R^1$ is hydroxymethyl and Y is oxygen may be prepared by treatment of the corresponding compound wherein $R^1$ is halomethyl with an inorganic alkali metal hydroxide, such as aqueous sodium hydroxide. The compounds of Formula (I) wherein $R^1$ is hydroxymethyl and Y is oxygen or sulfur may be prepared by hydrolysis of the corresponding compound wherein $R^1$ is alkanoylmethyl.

The compounds of Formula (I) wherein $R^2$ is chloro or bromo are generally prepared by chlorinating or brominating the corresponding compound wherein $R^2$ is hydrogen with a chlorinating or brominating agent such as N-bromosuccinimide or N-chlorosuccinimide by conventional procedures, as depicted in the following equation (4):

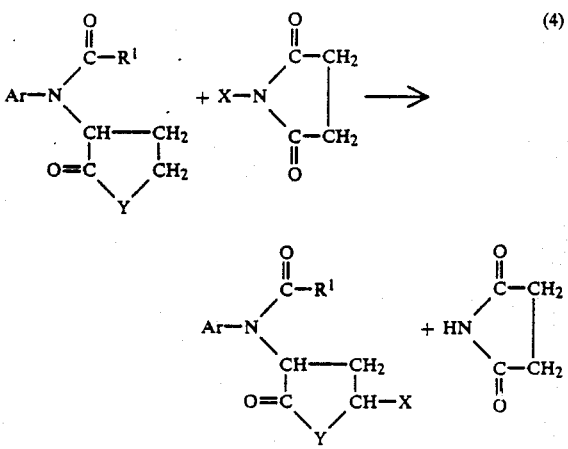

wherein Ar, $R^1$, Y and X are as previously defined.

UTILITY

The compounds of the invention are useful for controlling fungi, particularly plant fungal infections. However, some fungicidal compositions of the invention may be more fungicidally active than others against particular fungi. For example, the activity of the preferred compounds of the invention is highly specific for certain fungal diseases such as downy mildews, e.g., *Plasmopara viticola* (grapes) and *Peronospora parasitica* (cabbage and collard), late blights, e.g., *Phytophthora infestans* (tomatoes and potatoes), and crown and root rots, e.g. Phytophthora.

The compounds of the invention are particularly useful fungicides because they cure established fungal infections. This permits economical use of the fungicides of the invention, because they need not be applied to plants unless fungal infection actually occurs. Thus, a preventative program of applying fungicides against potential fungal infection is not necessary.

When used as fungicides, the compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5-80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of longchain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

The preparation and fungicidal activity of the compounds of the invention is illustrated by the following examples.

EXAMPLE 1

Preparation of
3-(N-chloroacetyl-N-2,6-dimethylphenyl)-gamma-butyrothiolactone

A solution of 10 g (0.055 mol) alpha-bromo-gamma-butyrothiolactone, 6.68 g (0.055 mol) 2,6-dimethylaniline and 5.58 g (0.055 mol) dimethylpyridine was heated at 85°–90° C. for 12 hours. The reaction mixture was then cooled, diluted with water and dichloromethane. The organic phase was separated and filtered through a short silica gel column. The filtrate was evaporated under reduced pressure to give an oil residue. The residue was washed with 5% aqueous hydrochloric acid solution, washed with water, and dried over magnesium sulfate to give 7.2 g of 3-(N-dimethylphenylamino)-gamma-butyrothiolactone. The infrared spectrum of the thiolactone product showed strong carbonyl absorption at 5.88 micron. Elemental analysis for $C_{12}H_{15}NOS$ showed: %S, calc. 14.5, found 14.2.

A solution of 1.52 g (0.0134 mol) chloroacetyl chloride in 10 ml toluene was added dropwise to a solution of 2.97 g (0.0134 mol) 3-(N-dimethylphenylamino)-gamma-butyrothiolactone in 100 ml benzene maintained at reflux temperature. The reaction mixture was heated at reflux until the evolution of hydrochloride gas ceased (about 3 hours), cooled, and evaporated under reduced pressure to give a brown solid. Recrystallization from isopropanol gave 2.5 g of 3-(N-chloroacetyl-N-2,6-dimethylphenylamino)-gamma-butyrothiolactone, as tan crystals, m.p. 138°–139° C. The infrared spectrum of the product showed two strong carbonyl absorption bands at 5.88 microns and 6.02 microns. The product is tabulated in Table A as Compound No. A-1.

EXAMPLE 2

Preparation of
3-(N-chloroacetyl-N-2-chloro-6-methylphenylamino)-gamma-butyrothiolactone A solution of 8 g (0.044 mol) alpha-bromo-gamma-butyrothiolactone, 6.23 g (0.044 mol) 2-chloro-6-methylaniline and 4.7 g (0.044 mol) 2,6-dimethylpyridine was heated for about 16 hours at about 95° C. under a nitrogen atmosphere. The reaction mixture was cooled, diluted with 60 ml dichloromethane, washed with water, washed with 10% aqueous hydrochloric acid, and filtered. The filtrate was dried over magnesium sulfate and evaporated under reduced pressure to give a dark viscous residue. The residue was eluted through a short silica gel chromatography column with dichloromethane. The product-containing fractions were stripped to give 4.59 g of 3-(N-2-chloro-6-methylphenylamino)-gamma-butyrothiolactone. Thin-layer chromatography of the product showed one large spot. The infrared spectrum of the product showed strong carbonyl absorption at 5.88 microns and the nuclear magnetic resonance spectrum showed a 3-proton singlet for the methyl group at 2.33 ppm (relative to tetramethylsilane).

A solution of 2.15 g (0.019 mol) chloroacetyl chloride in 10 ml toluene was added dropwise to a refluxing solution of 4.59 g (0.019 mol) 3-(N-2-chloro-6-methylphenylamino)-gamma-butyrothiolactone in 150 ml toluene. The reaction mixture was heated at reflux for about 7 hours (HCl was evolved), stirred about 16 hours at 25° C. and evaporated under reduced pressure to give a dark residue. Thin-layer chromatography of the residue showed two spots. The residue was chromatographed through a silica-gel column with acetone/dichloromethane elution. The chromatographic fractions containing the second material eluted from the column were combined and evaporated to give the desired product, which was crystallized from isopropyl alcohol to give 0.98 g of product, as a brown solid, m.p. 133°–137° C. The infrared spectrum of the product showed two strong carbonyl absorption bands at 5.84 microns and 5.95 microns. The compound is tabulated in Table A as Compound No. A-3.

EXAMPLE 3

Preparation of
3-(N-methoxymethyl-N-2,6-dimethylphenylamino)-gamma-butyrothiolactone A solution of 1.46 g (0.0135 mol) methoxyacetyl chloride in 10 ml dichloromethane was added dropwise to a refluxing solution of 3 g (0.0135 mol) 3-(N-2,6-dimethylphenyamino)-gamma-butyrothiolactone in 200 ml toluene. The reaction mixture was heated at reflux for 3 hours and evaporated to give a solid. The solid was recrystallized from a 10:1:10 solvent mixture of ether:benzene:hexane to give 1.8 g of the product, as a tan solid, m.p. 86°–87° C. The infrared spectrum of the product showed two strong carbonyl absorption bands at 5.85 microns and 6.03 microns. The product is tabulated in Table A as Compound No. A-4.

EXAMPLE 4

Preparation of
3-(N-chloroacetyl-N-2,6-dimethylphenylamino)-5-chloro-gamma-butyrolactone A slurry of 16 g (0.06 mol) of 3-(N-chloroacetyl-N-2,6-dimethylphenylamino)-gamma-butyrolactone, 11 g (0.08 mol) N-chlorosuccinimide and 0.5 g benzoyl peroxide in 200 ml carbon tetrachloride was heated under reflux for 18 hours. The reaction mixture was cooled to about 25° C. A solid separated. The solid was filtered from the reaction mixture and washed with 200 ml dichloromethane. The mother liquor was washed with water, dried over magnesium sulfate and evaporated under reduced pressure to give an oil residue. The residue was crystallized from ether to give 19.5 g of product, m.p. 103°–106° C. This product is tabulated in Table B as Compound No. B-1.

EXAMPLE 5

Preparation of
3-(N-acetoxyacetyl-N-2,6-dimethylphenylamino)-gamma-butyrolactone A 13.7-g (0.1-mcl) sample of acetoxyacetyl chloride was added dropwise to a solution of 20.5 g (0.1 mol) N-2,6-dimethylphenylamino-gamma-butyrolactone and 7.9 g (0.1 mol) pyridine in 150 ml benzene. After completion of the addition, the reaction mixture was stirred at about 25° C. for 4 hours, then washed with water, dried over magnesium sulfate and evaporated under reduced pressure to give an oily residue. The residue was crystallized from ethyl/hexane to give 27.3 g of product, m.p. 90°–91° C. This product is tabulated in Table B as Compound No. B-2.

3-(N-cyclopropylcarbonyl-N-2,6-dimethylphenylamino)-gamma-butyrolactone can be made in an analogous manner using cyclopropylcarbonyl chloride and N-2,6-dimethylphenylamino-gamma-butyrolactone as starting materials.

EXAMPLE 6

Preparation of
N-hydroxyacetyl-N-2,6-dimethylphenylamino-gamma-butyrolactone

A solution of 50 g (0.18 mol) 3-(N-chloroacetyl-N-2,6-dimethylphenylamino)-gamma-butyrolactone, 14.5 g (0.36 mol) sodium hydroxide dissolved in 50 ml water, and 450 ml dimethoxyethane was stirred at about 25° C. for 16 hours. The resulting reaction mixture was filtered, diluted with 500 ml dichloromethane. Hydrogen chloride gas was bubbled into the reaction mixture for 1 hour. The reaction mixture was filtered, dried over magnesium sulfate, and evaporated under reduced pressure. The residue was washed with 10% ethyl ether/90% hexane, filtered and air-dried to give 36.5 g of the product as a white crystalline solid, m.p. 173–174° C. The product is tabulated in Table B as Compound No. B-3.

EXAMPLE 7

Preparation of
N-ethoxyacetyl-N-2,6-dimethylphenylamino-gamma-butyrolactone

A 6.2-g (0.05-mol) sample of ethoxyacetyl chloride was added dropwise to a refluxing solution of 10.3 (0.05 mol) 3-(N-2,6-dimethylphenylamino)-gamma-butyrolactone in 150 ml toluene. The reaction mixture was then heated under reflux for 2 hours. After cooling, the reaction mixture was washed with water, washed with saturated sodium bicarbonate solution, washed with water, dried over magnesium sulfate and evaporated to give 11.2 g of 3-(N-ethoxyacetyl-N-2,6-dimethylphenylamino)-gamma-butyrolactone, m.p. 73°–75° C. The product is tabulated in Table B as Compound No. B-9.

EXAMPLE 8

Preparation of
N-methylthioacetyl-N-2,6-dimethylphenylamino-gamma-butyrolactone

A 22-g (0.3-mol) sample of sodium methylmercaptide was added in small portions to a solution of 25.3 g (0.08 mol) N-bromoacetyl-N-2,6-dimethylphenylamino)-gamma-butyrolactone, m.p. 116°–117° C., in 200 ml dimethyl sulfoxide. A mild exotherm ensued. The reaction mixture was allowed to stir at about 25° C. for about 16 hours. The reaction mixture was then heated to about 150° C. under reduced water aspirator pressure to remove a portion of the dimethyl sulfoxide solvent. The residue was diluted with water and the aqueous layer separated. The organic portion was dissolved in 350 ml dichloromethane, washed with water, dried over magnesium sulfate and evaporated under reduced pressure to give an oil. The oil was chromatographed through a silica gel column (20% acetone/80% petroleum ether elution) to give the product (11 g), which after crystallization from ethyl ether/acetone melted at 77°–78° C. The product is tabulated in Table B as Compound No. B-6.

EXAMPLE 9

Preparation of
3-(N-chloroacetyl-N-2-methylnaphth-1-ylamino)-gamma-butyrolactone A 200-ml round-bottom flask equipped with a heating mantle and connected to a water aspirator vacuum system was charged with 15.0 g (0.1 mcl) 1-amino-2-methylnaphthalene, 16.4 g (0.1 mol) alpha-bromo-gamma-butyrolactone and 10.7 g (0.1 mol) 2,6-dimethylpyridine. The reaction mixture was maintained at about 94°–101° C. and 160 mm of Hg for about 7 hours. The reaction mixture was cooled, diluted with 100 ml acetone and filtered. The filtrate was evaporated under reduced pressure to give an oily residue which was eluted through a silica gel column with 15% acetone/85% petroleum ether to give 14.6 g of 3-(N-2-methylnaphth-1-ylamino)-gamma-butyrolactone, m.p. 92°–94° C. Elemental analysis for $C_{15}H_{15}NO_2$ showed: %C, calc. 75.0, found 74.5; %H, calc. 5.9, found 5.6; %N, calc. 5.8, found 5.6.

A 2.4-g (0.021 mol) sample of chloroacetyl chloride was added to a refluxing solution of 5.0 g (0.021 mol) 3-(N-2-methylnaphth-1-ylamino)-gamma-butyrolactone in 100 ml toluene. The reaction mixture was heated under reflux for 30 minutes. Gas was evolved and a white precipitate formed during the 30-minute reflux period. The reaction mixture was cooled, washed with water, dried over magnesium sulfate and evaporated under reduced pressure to give 4.3 g of product, as a white solid, m.p. 121°–122° C. The infrared spectrum of the product showed two strong carbonyl absorption bands at 5.62 microns and 5.88 microns. The product is tabulated in Table C as Compound No. C-1.

EXAMPLE 10

Preparation of
3-(N-methoxymethyl-N-2-methylnaphth-1-ylamino)-
gamma-butyrolactone A 2.4 g (0.022 mol) sample of methoxyacetyl chloride was added dropwise to a solution of 5.5 g (0.022 mol) 3-(N-2-methylnaphth-1-ylamino)-gamma-butyrolactone and 1.7 g (0.022 mol) pyridine in 100 ml dichloromethane. The reaction mixture was stirred one hour at about 25° C. and then heated under reflux for 6 hours. After cooling overnight, the reaction mixture was washed successively with water, saturated sodium bicarbonate solution, water, dried over magnesium sulfate and evaporated under reduced pressure. The residue was chromatographed through a silica gel column. Elution with 25% acetone/75% petroleum ether gave 4.3 g of the product, m.p. 42°-46° C. The product is tabulated in Table C as Compound No. C-2.

The compounds tabulated in Tables A, B and C were prepared by procedures similar to those of Examples 1-10. The structure of each compound tabulated in Tables A, B and C was confirmed by nuclear magnetic resonance spectroscopy and/or infrared spectral analysis.

EXAMPLE 11

Preventative Tomato Late Blight

Compounds of the invention were tested for the preventative control of the Tomato Blight organism *Phytophthora infestans*. Five- to six-week-old tomato (cultivar Bonny Best) seedlings were used. The tomato plants were sprayed with a 250-ppm suspension of the test compound in acetone, water and a small amount of a nonionic emulsifier. The sprayed plants were then inoculated one day later with the organism, placed in an environmental chamber and incubated at 66°-68° F. and 100% relative humidity for at least 16 hours. Following the incubation, the plants were maintained in a greenhouse at 60-80% relative humidity for approximately 7 days. The percent disease control provided by a given test compound was based on the percent disease reduction relative to untreated check plants. The results are tabulated in Table I. In Table I, the test concentration is 250 ppm unless otherwise indicated by the figures in parentheses.

EXAMPLE 12

Eradicant Tomato Late Blight Control

Several compounds of the invention were tested for the eradicant control of the Tomato Late Blight organism *Phytophthora infestans*. Five- or six-week-old tomato (cultivar Bonny Best) plants were used. The tomato plants were inoculated with the organism, placed in an environmental chamber and incubated at 18°-22° C. and 100% relative humidity for 2 days. The plants were then sprayed with a 250-ppm suspension of the test compound in acetone, water and a small amount of a nonionic emulsifier. The sprayed plants were allowed to dry and then were maintained in a greenhouse at 18°-22° C. and at 95-100% relative humidity. Seven days after inoculation, the plants were observed for fungal infections. The amount of disease control provided by a given test compound was based on the amount of disease reduction relative to untreated check plants. The results are tabulated in Table I. In Table I, the test concentration is 250 ppm unless otherwise indicated by the figures in parentheses.

EXAMPLE 13

Preventative Grape Downy Mildew Control

The compounds of the invention were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 18°-22° C. and about 100% relative humidity. Seven to nine days after inoculation, the amount of disease control was determined. The percent disease control provided by a given test compound was based on the percent disease reduction relative to untreated check plants. The results are tabulated in Table I.

EXAMPLE 14

Eradicant Grape Downy Mildew Control

The compounds of the invention were tested for the eradicant control of the grape downy mildew organism *Plasmopara viticola*. Detached leaves of between 70 and 85 mm diameter of 7-week-old *Vitis vinifera* cultivar Emperor grape seedlings were used as hosts. The leaves were inoculated with the organism and placed in an environmental chamber and incubated at 18°-22° C. and at about 100% relative humidity for 2 days. The leaves were then sprayed with a solution of the test compound in acetone. The sprayed leaves were then maintained at 18°-22° C. and at about 100% relative humidity. Seven to nine days after inoculation, the amount of disease control was determined. The product disease control provided by a given test compound was based on the percent disease reduction relative to nontreated check plants. The results are tabulated in Table I.

EXAMPLE 15

Systemic Soil Drench Treatment for Safflower Crown and Root Rot Control

Compound B-4 (4-methoxyacetyl-N-2,6-dimethylphenyl-amino-gamma-butyrolactone) was tested to determine its systemic activity in soil-drench applications against the safflower crown and root rot organisms, *Phytophthora cryptogea* and *P. parasitica*.

Two-week-old safflower seedlings were used as hosts. Pots containing the seedlings were drenched with an aqueous suspension of the test compound at various test concentrations (four pots per concentration level). One day after treatment a spawn of the organism was poured on the soil surface in the pots. The spawn was prepared by cultivating the organism in a mixture of oat flakes, potato dextrose and soil. The inoculated seedlings were then maintained in a greenhouse at 20°-25° C. day and 15°-20° C. night temperature. Three to four weeks after inoculation, the plant roots and crown were rated for disease. The percent disease control provided by the test compound was based on percent disease reduction relative to non-treated check plants. The test concentrations and the percent disease control are tabulated in Table II.

TABLE A

Compounds of the Formula

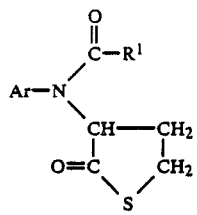

| No. | Ar | $R^1$ | Melting Point, °C. | Cl Calc. | Cl Found | S Calc. | S Found |
|---|---|---|---|---|---|---|---|
| A-1 | 2,6-$(CH_3)_2\phi$ | $ClCH_2$ | 130–131 | 11.9 | 13.1 | 10.8 | 11.7 |
| A-2 | 2,6-$(CH_3)_2\phi$ | $CH_3CO_2CH_2$ | 124–125 | — | — | 10.0 | 10.2 |
| A-3 | 2-Cl—6-$CH_3\phi$ | $ClCH_2$ | 133–137 | 22.3 | 23.6 | 10.0 | 11.0 |
| A-4 | 2,6-$(CH_3)\phi$ | $CH_3CCH_2$ | 86–87 | — | — | 10.9 | 11.2 |
| A-5 | 2-Cl—6-$CH_3\phi$ | $CH_3CO_2CH_2$ | 99–100 | 10.4 | 11.7 | 9.4 | 9.1 |
| A-6 | 3,4-$(Cl)_2\phi$ | $ClCH_2$ | oil | 31.5 | 32.7 | 9.4 | 9.3 |
| A-7 | 2,6-$(C_2H_5)_2\phi$ | $ClCH_2$ | 108–114 | 10.9 | 12.6 | 9.8 | 10.3 |
| A-8 | 2,6-$(C_2H_5)_2\phi$ | $CH_3CCH_2$ | 74–82 | — | — | 10.0 | 10.6 |
| A-9 | 2,3-$(CH_3)_2\phi$ | $ClCH_2$ | 99–102 | 11.9 | 11.7 | 10.8 | 10.2 |
| A-10 | 2,3-$(CH_3)_2\phi$ | $CH_3OCH_2$ | oil | — | — | 10.9 | 10.3 |
| A-11 | 2-$CH_3$—6-$C_2H_5\phi$ | $ClCH_2$ | 110–120 | 57.8 | 57.8[1] | 5.8 | 5.8[2] |
| A-12 | 2-$CH_3$—6-$C_2H_5\phi$ | $CH_3OCH_2$ | 88–90 | 62.4 | 52.5[1] | 6.8 | 6.8[2] |
| A-13 | 2,3,6-$(CH_3)_3\phi$ | $CH_3OCH_2$ | 101–103 | 62.5 | 60.2[1] | 6.8 | 6.7[2] |
| A-14 | 2,3,6-$(CH_3)_3\phi$ | $ClCH_2$ | 104–107 | 57.8 | 56.5[1] | 5.8 | 5.8[2] |
| A-15 | 2,3,5,6-$(CH_3)_4\phi$ | $ClCH_2$ | 140–143 | 59.0 | 60.1[1] | 6.1 | 6.3[2] |
| A-16 | 2,3,5,6-$(CH_3)_4\phi$ | $CH_3OCH_2$ | 122–123 | 63.6 | 65.8[1] | 7.2 | 7.4[2] |

[1]Carbon
[2]Hydrogen
$\phi$ = Phenyl

TABLE B

Compounds of the Formula

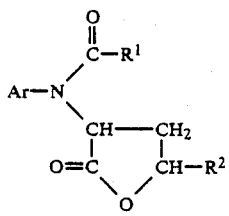

| No. | Ar | $R^1$ | $R^2$ | m.p., °C. | C Cal. | C Fd. | H Cal. | H Fd. | N Cal. | N Fd. | X Cal. | X Fd. |
|---|---|---|---|---|---|---|---|---|---|---|---|---|
| B-1 | (1) | $ClCH_2$ | Cl | 103–106 | — | — | — | — | — | — | 22.4 | 21.0[1] |
| B-2 | (1) | $CH_3CO_2CH_2$ | H | 90–91 | 63.0 | 63.3 | 6.3 | 6.7 | 4.6 | 4.5 | — | — |
| B-3 | (1) | $HOCH_2$ | H | 173–174 | 63.9 | 63.2 | 6.5 | 6.6 | 5.3 | 4.4 | — | — |
| B-4 | (1) | $CH_3OCH_2$ | H | 133–134 | 65.0 | 65.5 | 6.9 | 6.8 | 5.1 | 5.2 | — | — |
| B-5 | (1) | $\phi SCH_2$ | H | 84–86 | — | — | — | — | — | — | 8.9 | 9.0[2] |
| B-6 | (1) | $CH_3SCH_2$ | H | 77–78 | — | — | — | — | — | — | 10.9 | 9.1[2] |
| B-7 | (2) | $ClCH_2$ | H | oil | — | — | — | — | — | — | 9.2 | 11.1[1] |
| B-8 | (2) | $CH_3OCH_2$ | H | oil | 67.0 | 66.0 | 7.2 | 7.2 | 4.8 | 4.0 | — | — |
| B-9 | (1) | $CH_3CH_2OCH_2$ | H | 73–75 | 66.0 | 66.0 | 7.3 | 7.2 | 4.8 | 5.0 | — | — |
| B-10 | (3) | $ClCH_2$ | H | 128–130 | — | — | — | — | — | — | 11.5 | 13.2[1] |
| B-11 | (3) | $CH_3OCH_2$ | H | 104–105 | 66.9 | 67.5 | 7.5 | 7.5 | 4.6 | 4.5 | — | — |
| B-12 | (1) | $i$-$C_3H_7OCH_2$ | H | oil | 66.9 | 66.9 | 7.6 | 7.5 | 4.6 | 4.1 | — | — |
| B-13 | (1) | $ClCH_2$ | Br | 98–102 | 46.6 | 47.7 | 4.2 | 4.4 | 3.9 | 4.2 | — | — |

(1) 2,6-$(CH_3)_2)\phi$
(2) 2,3,6-$(CH_3)_3\phi$
(3) 2,3,4,5-$(CH_3)_4\phi$

[1]Chlorine
[2]Sulfur

TABLE C

Compounds of the Formula

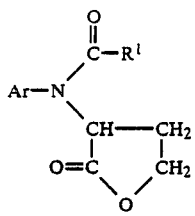

| No. | Ar | R¹ | Melting Point, °C. | C Cal. | C Fd. | H Cal | H Fd. | N Cal | N Fd. | X Cal. | X Fd. |
|---|---|---|---|---|---|---|---|---|---|---|---|
| C-1 | (1) | ClCH₂ | 121–122 | — | — | — | — | — | — | 11.2 | 12.5(Cl) |
| C-2 | (1) | CH₃OCH₂ | 42–46 | 69.0 | 72.6 | 6.1 | 6.6 | 4.5 | 4.5 | — | — |
| C-3 | (1) | BrCH₂ | 116–118 | — | — | — | — | — | — | 22.1 | 21.5(Br) |
| C-4 | (1) | CH₃SCH₂ | 52–55 | 65.6 | 62.3 | 5.8 | 5.4 | — | — | — | — |
| C-5 | (2) | ClCH₂ | 110–113 | 63.3 | 63.3 | 4.7 | 4.8 | 4.6 | 4.5 | — | — |
| C-6 | (2) | CH₃OCH₂ | 109–111 | 68.2 | 69.6 | 5.7 | 5.9 | 4.7 | 5.3 | — | — |

(1) 1-(2-methylnaphthyl)
(2) 1-(naphthyl)

TABLE I

| | % Control | | | |
|---|---|---|---|---|
| | Tomato Late Blight | | Grape Downy Mildew | |
| No. | Preventative (ppm) | Eradicative (ppm) | Preventative (ppm) | Eradicative (ppm) |
| A-1 | 98 | 84 (100) | 82 (40) | 5 (100) |
| A-2 | 14 | — | — | 3 (100) |
| A-3 | 100 | 42 (100) | — | 7 (100) |
| A-4 | 96 (40) | 81 (100) | 98 (100) | 10 (100) |
| A-5 | 29 | — | — | 0 (100) |
| A-6 | 23 | — | — | 0 (100) |
| A-7 | 98 | 54 | 93 (16) | 80 (16) |
| A-8 | 26 (100) | — | — | 0 (100) |
| A-9 | 68 (40) | — | — | 12 (100) |
| A-10 | 89 (100) | 95 | — | 80 (100) |
| A-11 | 80 | — | — | — |
| A-12 | 89 | — | — | — |
| A-13 | 100 | — | — | — |
| A-14 | 100 | — | — | — |
| A-15 | 37 | — | — | — |
| A-16 | 100 | — | — | — |
| B-1 | 100 | 92 (100) | 0 (100) | 88 (100) |
| B-2 | 88 | — | — | 9 (100) |
| B-3 | 92 (100) | 92 (100) | — | 0 (100) |
| B-4 | 88 (16) | 96 (40) | 100 (40) | 95 (16) |
| B-5 | 84 | 58 | — | 73 (100) |
| B-6 | 97 | 96 | — | 54 (100) |
| B-7 | 77 | — | — | — |
| B-8 | 100 | 93 (100) | — | — |
| B-9 | 97 | — | — | — |
| B-10 | 37 | — | — | — |
| B-11 | 100 | — | — | — |
| B-12 | 95 | — | — | — |
| C-1 | 100 | 55 (100) | 96 (16) | 84 (16) |
| C-2 | 0 | — | — | — |

TABLE II

Safflower Crown and Root Rot Control by Soil Drench

| Compound | Conc. ppm | % Control P. Cryptoqea | % Control P. Parasitica |
|---|---|---|---|
| Compound B-4 | 100* | 98 | 100 |
| | 40 | 78 | 100 |
| | 16 | 14 | 97 |
| Standard** (5-ethoxy-3-trichloromethyl-1,2,4-thiadiazole) | 100 | 78 | 98 |
| | 40 | 12 | 78 |
| | 16 | 0 | 17 |

*100 ppm = 50 micrograms/cm² = 4.46 lbs/acre
**U.S. Pat. Nos. 3,260,588 and 3,260,725

What is claimed is:

1. A compound of the formula

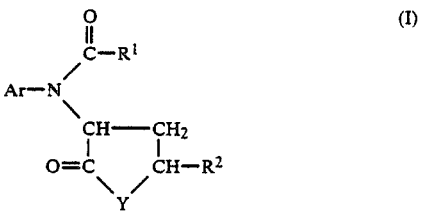

wherein Ar is phenyl, naphthyl, or phenyl or naphthyl substituted with 1 to 4 of the same or different substituents selected from fluoro, chloro, bromo, alkyl of 1 to 4 carbon atoms or alkoxy of 1 to 4 carbon atoms; R¹ is hydroxymethyl, halomethyl of 1 to 3 of the same or different halogens selected from fluoro, chloro, bromo, cycloalkyl of 3 to 6 carbon atoms, cycloalkyl of 3 to 6 carbon atoms substituted with 1 to 4 of the same or different substituents selected from alkyl of 1 to 4 carbon atoms, fluoro, chloro, bromo, hydroxy or alkoxy of 1 to 4 carbon atoms; and R² is hydrogen, chloro, bromo, alkyl of 1 to 6 carbon atoms, phenyl or phenyl substituted with 1 to 2 of the same or different substituents selected from fluoro, chloro, bromo and alkyl of 1 to 6 carbon atoms; and Y is O, with the proviso that when Ar is phenyl or substituted phenyl R¹ is not halomethyl, and with the further proviso that R¹ is not cyclopropyl.

2. The compound of claim 1 represented by the formula

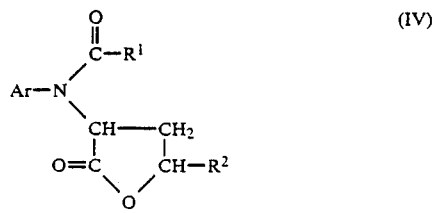

wherein Ar is phenyl or substituted phenyl as defined in claim 1, R² has the same significance as defined in claim 1, and R¹ is hydroxymethyl.

3. The compound of claim 1 represented by the formula

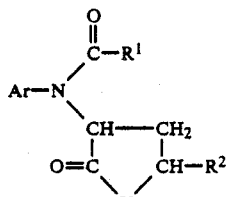

(VI)

wherein Ar is naphthyl or substituted naphthyl as defined in claim 1, and $R^1$, $R^2$ and Y have the same significance as defined in claim 1.

4. The compound of claim 1 represented by the formula

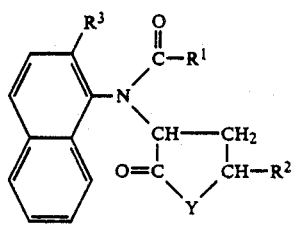

(VII)

wherein $R^1$ is chloromethyl; $R^3$ is hydrogen or alkyl of 1 to 3 carbon atoms; and Y is oxygen.

5.

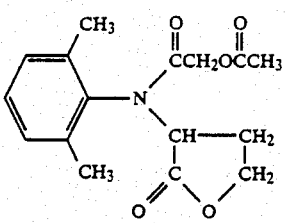

wherein Ar is phenyl, naphthyl, or phenyl or naphthyl substituted with 1 to 4 of the same or different substituents selected from fluoro, chloro, bromo, alkyl of 1 to 4 carbon atoms or alkoxy of 1 to 4 carbon atoms; $R^1$ is hydroxymethyl; and $R^2$ is hydrogen or alkyl of 1 to 6 carbon atoms.

6. A compound having the formula

7. A fungicidal composition comprising as active ingredient an effective fungicidal amount of the compound of claim 6, together with a biologically inert carrier.

8. A process for controlling fungi which process comprises application of a fungicidally effective amount of the compound of claim 6 to the plants or to a locus liable to be infected by said fungi.

9. A method for controlling the growth of *Phytophthora infestans* fungi which comprises appling to said fungi or their habitats a fungicidally effective amount of a compound of the formula defined in claim 1.

10. A method for controlling the growth of *Plasmopara viticola* fungi which comprises applying to said fungi or their habitats a fungicidally effective amount of a compound of the formula defined in claim 1.

* * * * *